United States Patent [19]

Baeckström

[11] Patent Number: 5,378,361
[45] Date of Patent: Jan. 3, 1995

[54] AXIALLY ADJUSTABLE CHROMATOGRAPHY COLUMN

[76] Inventor: Peter Baeckström, Larsbergsvägen 24, S-181 39 Lidingö, Sweden

[21] Appl. No.: 140,208
[22] PCT Filed: May 6, 1992
[86] PCT No.: PCT/SE92/00295
§ 371 Date: Dec. 28, 1993
§ 102(e) Date: Dec. 28, 1993
[87] PCT Pub. No.: WO92/19346
PCT Pub. Date: Nov. 12, 1992

[30] Foreign Application Priority Data

May 8, 1991 [SE] Sweden .................. 9101396-1

[51] Int. Cl.⁶ ........................... B01D 15/08
[52] U.S. Cl. ..................... 210/198.2; 210/656
[58] Field of Search ........... 210/656, 198.2, 450; 96/101, 106

[56] References Cited

U.S. PATENT DOCUMENTS

| | | |
|---|---|---|
| 4,510,058 | 4/1985 | Cais .................. 210/198.2 |
| 4,636,315 | 1/1987 | Allen ................. 210/656 |
| 4,737,292 | 4/1988 | Ritacco ............... 210/198.2 |
| 4,797,209 | 1/1989 | Jackson ............... 210/656 |
| 4,865,728 | 9/1989 | Larsson ............... 210/198.2 |
| 4,888,112 | 12/1989 | Kronwald ............. 210/198.2 |
| 4,927,531 | 5/1990 | Sakamoto ............. 210/198.2 |
| 5,141,635 | 2/1992 | Le Plang ............. 210/198.2 |
| 5,188,730 | 2/1993 | Kronwald ............. 210/198.2 |
| 5,213,683 | 5/1993 | Mann ................. 210/198.2 |

FOREIGN PATENT DOCUMENTS 509591 8/1970 Switzerland ............ 210/198.2

Primary Examiner—Ernest G. Therkorn
Attorney, Agent, or Firm—Pravel, Hewitt, Kimball & Kreiger

[57] ABSTRACT

Described is a column for separation of substance mixtures with a liquid. A cylindrical tube has a closure at each end. At least one of the closures is a movable piston. The piston has a socket which is radially expandable by axial pressing of two interacting conical parts for sealing of the piston against the inner wall of the column.

4 Claims, 1 Drawing Sheet

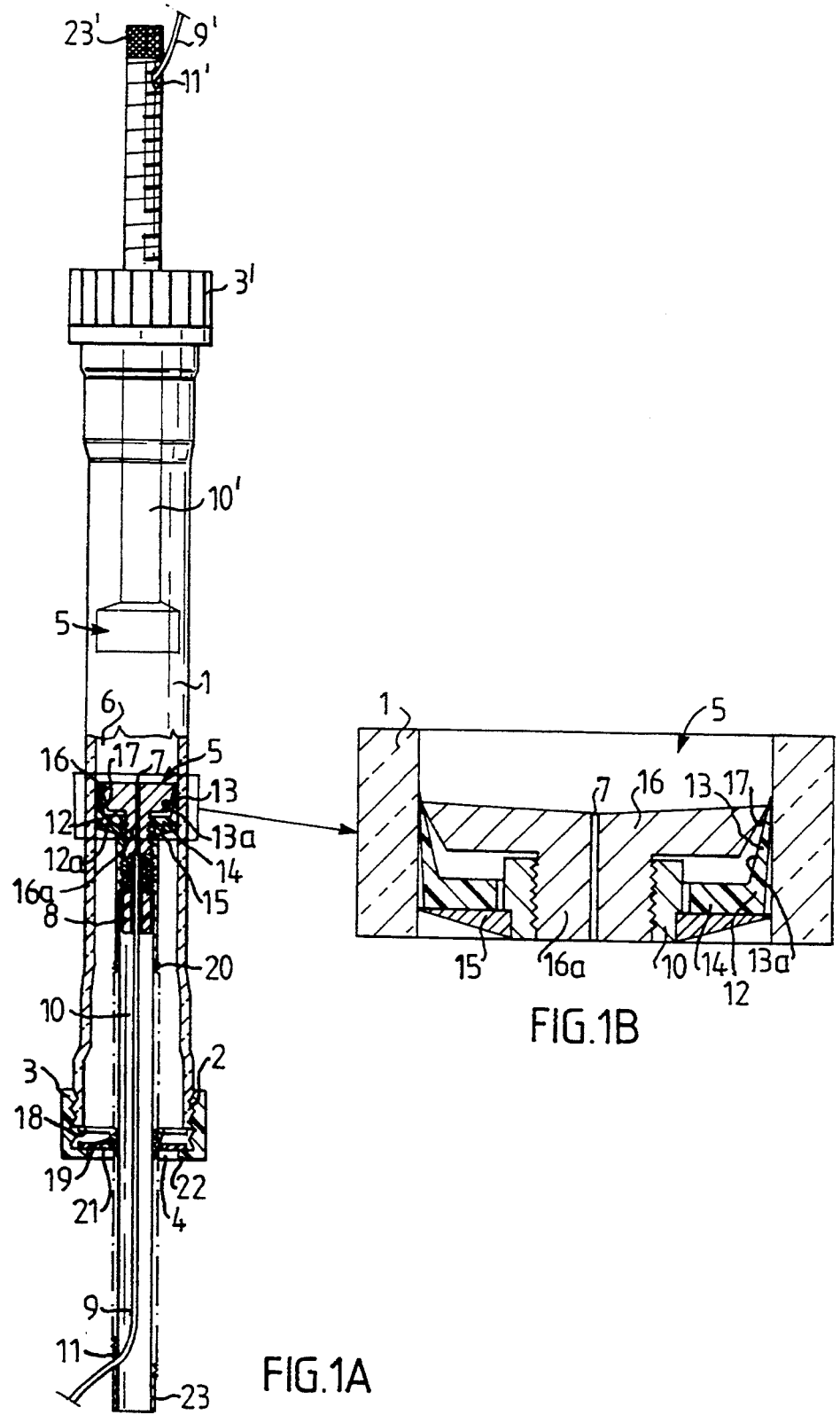

AXIALLY ADJUSTABLE CHROMATOGRAPHY COLUMN

The present invention relates to a column for separation of substance mixtures, preferably on a preparative scale, with a liquid medium.

Liquid chromatography is used for separation of mixtures of substances. Thereby, such mixture is introduced in a column filled with an adsorptive agent, whereupon a liquid, referred to as an eluent, is allowed to flow through the column. Separation is achieved by the components of the mixture being retarded to a different degree by the adsorptive agent. Liquid chromatography is used for preparative *or analytical purposes. For analytical purposes, the substance mixture is introduced in the column in a liquid phase, whereupon an eluent is allowed to flow through the column and into a detector which records the amount of passing substance.

Preparative chromatography is carried out with the purpose of producing pure compounds, or isolating compounds from a mixture of substances. The amount of substance which is introduced into the column for such purpose is one to several powers of ten greater than what is introduced into a column for analytical purposes.

In preparative chromatography, in cases where the substance mixture is dissolved in a suitable liquid, the mixture may be introduced into the column via tubing connected to the end of the column. In other cases, the substance mixture is introduced in a solid phase. A standard procedure is to adsorb the mixture, in a separate operation, on an appropriate adsorbent material, which is thereafter introduced into the column on top of the adsorptive agent. The substance mixture may comprise synthetic products or natural products, e.g. plant extracts. Traditionally, long columns are used in this context, the top end of which is open. The column is packed with an adsorptive agent to a certain level, followed by the substance mixture. The uppermost part of the column is used as a reservoir for the eluent, which is allowed to pass through the adsorptive agent with the aid of gravity. This type of column allows for continuous supply of eluent. When higher flow rates are desired, than what can be achieved with a hydrostatic pressure alone, the eluent may be forced through the column by closing the top end of the column and applying gas pressure. The latter method, as currently applied, is referred to as "flash chromatography". Although this is an inexpensive solution, the method has drawbacks. Glass columns may explode by too high pressures applied, with the risk of glass splinter flying about, and further, the system has to be decompressed on filling or exchange of eluent. Decompression can cause formation of blisters whereby inhomogenities occur in the packing of the adsorptive agent.

Forcing of the eluent through the column with a pump bids great advantages. Supply of eluent and change of composition of the eluent can be done in a continuous manner on the suction side of the pump. With medium pressures, the compressibility of the liquid is negligible. Due to this, the risk of glass splinter flying about on breakage is small in use of columns which completely filled up with solid phase and liquid. Due to said fact, it is advantageous to supply the eluent to the column through a hollow piston, which can be brought into close contact with the adsorptive material, whereupon it is made to seal against the wall of the column.

This type of chromatography is sometimes referred to as medium pressure chromatography, which is carried out at a pressure up to a few tens of bar, e.g. 4 bar (0.4 MPa). Several manufacturers supply columns where requirements of sealing against the column walls are complied with. In many instances, columns are employed, designed as a cylinder of relatively thick glass (2–8 mm) wherein the length of the column may be made adjustable by means of a piston in the column. Usually the inlet or outlet of the column runs through the piston and piston shaft in flexible tubing which exits at the end of the piston shaft, alternatively a tube is provided having a connection for flexible tubing opening at the end thereof. Usually the piston is provided with a device which prevents it from rotating during compression of the O-ring.

Numerous inconveniences occur with this type of design. If the O-ring is compressed too strongly, the column may rupture. If the piston shaft is made of plastic material, too hard tightening of the screw may cause the piston shaft to break or the compression threads to be damaged. Further, a dead lumen occurs between the lowermost part of the piston and the O-ring. A problem with such a column is that, on use of aggressive liquid media, certain organic solvents in particular, the O-ring may be affected and cause leakage and contamination of the liquid medium. As most columns on the market are intended for biochemical separations, no particular attention has been paid, in choice of material for the constructive details, to resistance against solvents such as chloroform, methylene chloride and ethyl acetate, which are usually occurring eluents in organic chemistry. These solvents may cause the O-ring to swell, which may bring about rupture of the column or render the piston difficult to remove. A column provided with the mentioned O-ring seal, where the piston shaft is made of plastic material has been supplied by Amicon Ltd. Upper Mill, Stonehouse, Gloustershire GL 10 2BJ, GB.

Pharmacia LKB Biotecnology, Sweden have supplied a column named SR Column System, which, in the place of an O-ring employs a piston having a conical outer surface, and a ring arranged around said piston having a conical inner surface, where the conical surfaces are pressed against each other with a similar mechanism as in the column having the O-ring seal, thus that the ring will seal against the column wall. In this column it appears that the conical surfaces have the same cone angle, and the piston is locked in the column from the outset. With this construction, the ring has to be strongly tightened initially, to avoid leakage. Thereby, like in the column having the O-ring seal, a risk occurs of rupture of the column wall. Columns of the previously known kinds are further impaired with the problem of a dead volume around the periphery of the upper end of the piston.

According to the present invention, these drawbacks are avoided in a column for separation of substance mixtures with a liquid medium, comprising a cylindrical tube with a separation space therein having a closure at each end, whereby the separation space has an inlet and an outlet, respectively, through a channel in each end thereof, whereby at least one of the closures is a movable piston trough which one of said channels runs and together with a channel in a piston shaft connected to the piston makes up the inlet or the outlet, whereby said piston has a socket which is radially expandable by axial pressing of two interacting conical parts, for sealing of the piston against the inner wall of the column. The invention is characterized in, that the piston comprises an expandable socket abutting, in its resting position, against the inner cylindrical surface of the column, and having a conical opening, widening towards the separation space with a certain cone angle, that the piston further comprises an inner part having an outer surface conically tapering in the direction away from the separation space and abutting with its periphery against the periphery of the conical opening, that said inner part has a cone angle greater than the cone angle of the expandable socket, which inner part can be pressed against the expandable collar, by tightening means operable from the outside of the column, to cause a first expansion thereof, and that the channelled piston shaft is lockable against the column by a locking means having a certain resilience in the longitudinal direction of the column, and that said resilience is arranged thus that it allows for pressing said inner part back under the action of the pressure of a liquid in the separation space, to achieve a further expansion of the expandable socket, to sealing against the column wall.

By "cone angle" is intended the top angle between the generatrices of the imagined full conical surfaces in which the respective conical surface is comprised, in an unloaded state. The angle of the respective conical surface to the column wall is half the cone angle.

The expandable socket can be made with a bottom, and/or a washer or similar device may be placed between the expandable part and the piston shaft. The inner part of the piston is designed in such way that, when pressed against the expandable socket, it is not locked against the bottom thereof, the washer or the end of the piston shaft, respectively.

While the tightening means, operable from the outside, can consist of a screw means arranged at the outer end of the piston shaft, as described above as known, in a preferred embodiment of the invention, the tightening means, operable from the outside is a thread means arranged between the inner part of the piston and the piston shaft, which is operable by turning the piston shaft.

In a further preferred embodiment of the invention, the locking means having a certain resilience is a fitting threadable onto the column or an equivalent holding means, such as a snap device, holding a lid having a built-in elasticity, which lid secures the piston shaft via securing means. In the case where the channel in the piston shaft is a tubing connected to the channel of the piston, it is preferred that the tubing outside the column runs through an opening arranged in the side of the piston shaft. In all columns on the market the inlet and outlet tubing exits concentrically with the piston shaft, i.e. trough the outermost end of the piston shaft, or is connected to the outer end of the piston shaft tube. This is disadvantageous, since the tubing will be folded and damaged if the column is lowered against a support surface during packing of the column. In the present invention, the inlet or outlet tubings are run out at the side of the piston shaft tube through a hole intended therefor, close to the outer end of the piston shaft tube. By this arrangement, the column may be supported on the piston shaft tube on packing of the column, without the tubing being damaged. With such arrangement, further, arrangement of a rotation device at the lower end of the piston shaft is facilitated.

BRIEF DESCRIPTION OF THE DRAWINGS

The invention is more closely described with reference to the enclosed drawing, showing a column according to an embodiment of the invention, partly in side view, partly in section (FIG. 1A) and a partial enlargement (FIG. 1B).

DESCRIPTION OF THE PREFERRED EMBODIMENTS

The column shown in the drawing comprises a column tube made of glass, having external threads at one end thereof and similar threads, not shown, at the other end of the column tube. The threads each engage a threaded cap 3,3'. An opening is shown in the planar end of the cap 3. In the column tube, a piston 5 and a similar piston 5' are movable. The pistons together delimit a separation space 6, the volume of which is variable by displacement of either or both pistons. In the piston 5 a channel 7 opens, which may be an outlet or an inlet, referred to here as an outlet channel. Said channel continues via a plug 8 in which a tubing 9 is attached, which is a continuing portion of the outlet channel. A similar inlet channel, not shown, in the piston 5' is connected to a tubing 9'. Tubing 9, 9' runs through a piston shaft 10, 10', and exits through a hole 11, 11' arranged in the side of the piston shaft.

The piston 5 comprises an expandable part 12, made of elastic material such as polytetrafluorethene. Part 12 comprises a collar 13, the periphery of which abuts against the inner surface of the column tube. Collar 13 has an inner surface 13a conically opening with a certain cone angle, e.g. 15° in a column having an inner diameter of 15 mm, and 34° in a column having an inner diameter of 30 mm, and a bottom part 14 integrated with the collar. Via a washer 15 the expandable part 12 is supported against the end of the piston shaft 10 directed towards the separation space. An inner part 16 of the piston 5 has a conical outer surface 17, tapering conically in the direction away from the separation space, said conical outer surface having a greater cone angle, e.g. 30° in a column having the diameter 15 mm and 50° in a column having the diameter 30 mm. The inner part 16 is attached via a threaded central tap 16a engaging an inner thread in the piston shaft. When the inner part 16 is forced into the expandable part 12, the conical surfaces 13a and 17 are brought into contact with each other, whereby part 12 is pressed against the column wall.

A slotted disk 18 has a conical central part 19, which has inner threads which by radial compression of the disk can be brought into engagement with threads 20 on the exterior of the piston shaft, by the conical part being pressed into a central opening in an elastically resilient disk 21, the periphery of which is supported against a flange 22 left by the opening 4 in the end of the cap 3. A optional knurled end 23, 23', which can be replaced by a through-going turning pin, is shown arranged on the end of the piston shaft 10, 10'.

A manner of using the column shown as an example is described in the following.

The piston 5, or 5' in the alternative, is adjusted to a desired position with the inner part 16 loosely abutting the collar 13. The cap 3 is screwed onto the threads 2, whereby the resilient disk 21 presses the central part 19 of the slotted disk into engagement of the threads 20. A first dilation of the collar 13 is brought about by turning the piston shaft 10, whereby the friction against the inner wall of the column tube 1 prevents parts 12 and 16 of the piston from rotating, at least to a maximal torque, at which rupture of the column is prevented by the piston starting to rotate. The maximal torque can be influenced by selection of material in the parts of the piston and selection of the area by which the collar 13 abuts the inner wall of the column. The separation space 2 is filled with an adsorptive agent and the second of pistons 5,5' is adjusted into a desired position and is locked in a similar manner as the first one. The mixture that is to be separated is filled via the inlet channel 9' (9 in the alternative). Eluent is introduced under an moderate overpressure through the inlet channel, and the liquid which flows out through the outlet channel is collected in fractions. The eluent exerts a pressure on the upper side of the inner part of the column. By the resilient disk allowing the piston shaft to move outwards, the inner part 16 of the piston is pressed into the expandable part 12, which expands. It is important that there is an open space 12a between the bottom part and the inner part of the piston, thus that expansion can be achieved in the two expansion phases.

While the column tube is normally made of glass, the expandable socket of the piston is preferably made of polytetrafluorethene or a similar polymer material inert against occurring solvents. The inner part of the piston, as well as the piston shaft and the supporting disk, when occurring, can be made of highly alloyed corrosion resistant steel, but strong polymer materials known for such purposes can also be employed, whereby care should be taken in order that the parts of the inner part touched by the liquid medium should be as inert against the liquid medium as is the expandable socket.

I claim:

1. A column for separation of substance mixtures with a liquid medium, comprising a cylindrical tube (1) with a separation space (6) therein having a closure at each end, whereby the separation space has an inlet and an outlet, respectively, through a channel (7,9) in each end thereof, whereby at least one of the closures is a movable piston (5) through which one of said channels runs and together with a channel in a piston shaft (10) connected to the piston makes up the inlet or the outlet, whereby said piston has a socket which is radially expandable by axial pressing of two interacting conical parts, for sealing of the piston against the inner wall of the column, wherein the piston (5) comprises an expandable socket (12) abutting, in its resting position, against the inner cylindrical surface of the column, and having a conical opening, widening towards the separation space with a certain cone angle, that the piston further comprises an inner part (16) having an outer surface conically tapering in the direction away from the separation space and abutting with its periphery against the periphery of the conical opening, that said inner part has a cone angle greater than the cone angle of the expandable socket, which inner part (16) can be pressed against the expandable collar, by tightening means operable from the outside of the column, to cause a first expansion thereof, and that the channelled piston shaft (10), arranged to the piston, is lockable against the column by a locking means (18) having a certain resilience in the longitudinal direction of the column, and that said resilience is arranged thus that it allows for pressing said inner part (16) back under the action of the pressure of a liquid in the separation space, to achieve a further expansion of the expandable socket (12), to sealing against the column wall.

2. A column according to claim 1, wherein the tightening means, operable from the outside, is a thread means (16a) arranged between the inner part of the piston and the piston shaft, which is operated by turning the piston shaft (10).

3. A column according to claim 1 or 2, wherein the locking means having a certain resilience is a fitting threadable onto the column and holding a lid (18) having a built-in elasticity, which lid secures the piston shaft via securing means (19).

4. A column according to claim 1 or 2, wherein the channel in the piston shaft is a tubing connected to the channel of the piston, the tubing outside the column runs through an opening (11) arranged in the side of the piston shaft.

* * * * *